United States Patent
Anselmi et al.

(10) Patent No.: US 11,848,085 B2
(45) Date of Patent: *Dec. 19, 2023

(54) METHODS AND SYSTEMS FOR MANAGING PRESCRIPTIONS

(71) Applicant: Express Scripts Strategic Development, Inc., St. Louis, MO (US)

(72) Inventors: Susan E. Anselmi, Nutley, NJ (US); Alexi E. Makarkin, Ballwin, MO (US); Samuel Affare, Florissant, MO (US); John W. Cooper, IV, St. Louis, MO (US); Jeffrey Whitworth, St. Charles, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/969,893

(22) Filed: Oct. 20, 2022

(65) Prior Publication Data

US 2023/0042725 A1 Feb. 9, 2023

Related U.S. Application Data

(63) Continuation of application No. 16/900,001, filed on Jun. 12, 2020, now Pat. No. 11,508,471.

(51) Int. Cl.
*G16H 20/10* (2018.01)
*G06Q 10/0832* (2023.01)
*G06Q 50/22* (2018.01)

(52) U.S. Cl.
CPC ......... *G16H 20/10* (2018.01); *G06Q 10/0832* (2013.01); *G06Q 50/22* (2013.01)

(58) Field of Classification Search
CPC ..... G16H 20/10; G06Q 10/0832; G06Q 50/22
See application file for complete search history.

(56) References Cited

U.S. PATENT DOCUMENTS

| 7,835,924 B1 | 11/2010 | Palazzolo |
| 7,856,363 B2 | 12/2010 | Palazzolo |

(Continued)

FOREIGN PATENT DOCUMENTS

| CA | 2860291 A1 * | 2/2015 | ............ G16H 20/10 |
| CA | 2860291 A1 | 2/2015 | |

OTHER PUBLICATIONS

Hwe, S.; Congdon, H.; Layson-Wolf, C.; Hose, B. "Characterizing medication synchronization programs within independent pharmacies." Journal of the American Pharmacists Association56.3: e86-e87. Elsevier. (May 2016-Jun. 2016) (Year: 2016).*

(Continued)

*Primary Examiner* — Linh Giang Le
(74) *Attorney, Agent, or Firm* — Husch Blackwell LLP

(57) ABSTRACT

Methods and systems for classifying and editing insurance claims records are described. In one embodiment, a method, which can be performed by a processor, includes determining that a first prescription drug prescribed to a first patient should be filled by a pharmacy, determining a first guidepost date and a second guidepost date related to the first prescription, determining a third guidepost date associated with a second prescription, comparing the third guidepost date to the first and second guidepost dates to determine whether the third guidepost date occurs after the first guidepost date and before the second guidepost date, and filling and dispensing the first prescription drug as a full prescription supply and the second prescription drug as a full prescription supply on the same dispense date when the third guidepost date occurs after the first guidepost date and before the second guidepost date.

28 Claims, 9 Drawing Sheets

(56) References Cited

U.S. PATENT DOCUMENTS

| | | | |
|---|---|---|---|
| 7,996,243 B1* | 8/2011 | Ali | G16H 10/60 |
| | | | 705/2 |
| 8,005,689 B2 | 8/2011 | Palazzolo | |
| 8,032,393 B2 | 10/2011 | Palazzolo et al. | |
| 8,050,942 B1 | 11/2011 | Ali | |
| 8,244,557 B1 | 8/2012 | Nadas | |
| 8,249,890 B1 | 8/2012 | Nadas | |
| 8,275,634 B2 | 9/2012 | Palazzolo | |
| 8,311,853 B1 | 11/2012 | Pankow | |
| 8,364,503 B1 | 1/2013 | Biesenthal | |
| 8,560,347 B1 | 10/2013 | Ali | |
| 8,666,776 B1 | 3/2014 | Nadas | |
| 8,670,995 B1 | 3/2014 | Nadas | |
| 2013/0090947 A1 | 4/2013 | Nockley | |
| 2016/0004841 A1 | 1/2016 | Power | |
| 2016/0103976 A1 | 4/2016 | Demogenes | |
| 2016/0110518 A1 | 4/2016 | Shelton | |
| 2016/0110519 A1 | 4/2016 | Louie | |
| 2017/0344724 A1 | 11/2017 | Nockley | |
| 2017/0372021 A9 | 12/2017 | Loiacono | |
| 2018/0075211 A1 | 3/2018 | Eng | |
| 2019/0267124 A1 | 8/2019 | Joplin | |
| 2020/0135318 A1 | 4/2020 | Miller | |

OTHER PUBLICATIONS http://gphabuzz.com/2014/11/get-a-letter-from-walgreens-about-med-sync-patents-heres-what-you-need-to-know/.

Johnson, http://www.drugstorenews.com/article/ateb-licenses-walgreens-entire-portfolio-prescription-alignment-patents,Jul. 10, 2014.

Johnson, http://www.drugstorenews.com/article/voiceport-licenses-11-walgreens-patents-field-prescription-alignment, Jul. 10, 2014.

Hiwe, et al., Characterizing medication synchronization programs within independent pharmacies, Journal of the American Pharmacists Associates 56.3: e86-e87, Elsevier (May 2016-Jun. 2016) (Year 2016).

Leslie, http://www.chaindrugreview.com/walgreens-licenses-prescription-management-patents/, Jul. 11, 2014.

* cited by examiner

METHODS AND SYSTEMS FOR MANAGING PRESCRIPTIONS

CROSS REFERENCE TO RELATED APPLICATIONS

This application is a continuation of U.S. application Ser. No. 16/900,001, which was filed Jun. 12, 2020. The entire disclosure of said application is incorporated herein by reference.

FIELD

The present disclosure relates generally to the technical field of data processing. In a specific example, the present disclosure may relate to managing requests.

BACKGROUND

Prescription Benefit Managers (PBM) take and fill thousands of prescription requests and prescription refills. Generally, PBMs receive these prescription requests as individual fill or refill submissions, leading to a large amount of processing to be performed by PBM servers and other host computers. Additionally, in a mail-order pharmacy setting, individualized prescription orders lead to a large burden on mail carriers and shipping companies.

DETAILED DESCRIPTION

Figure 1:
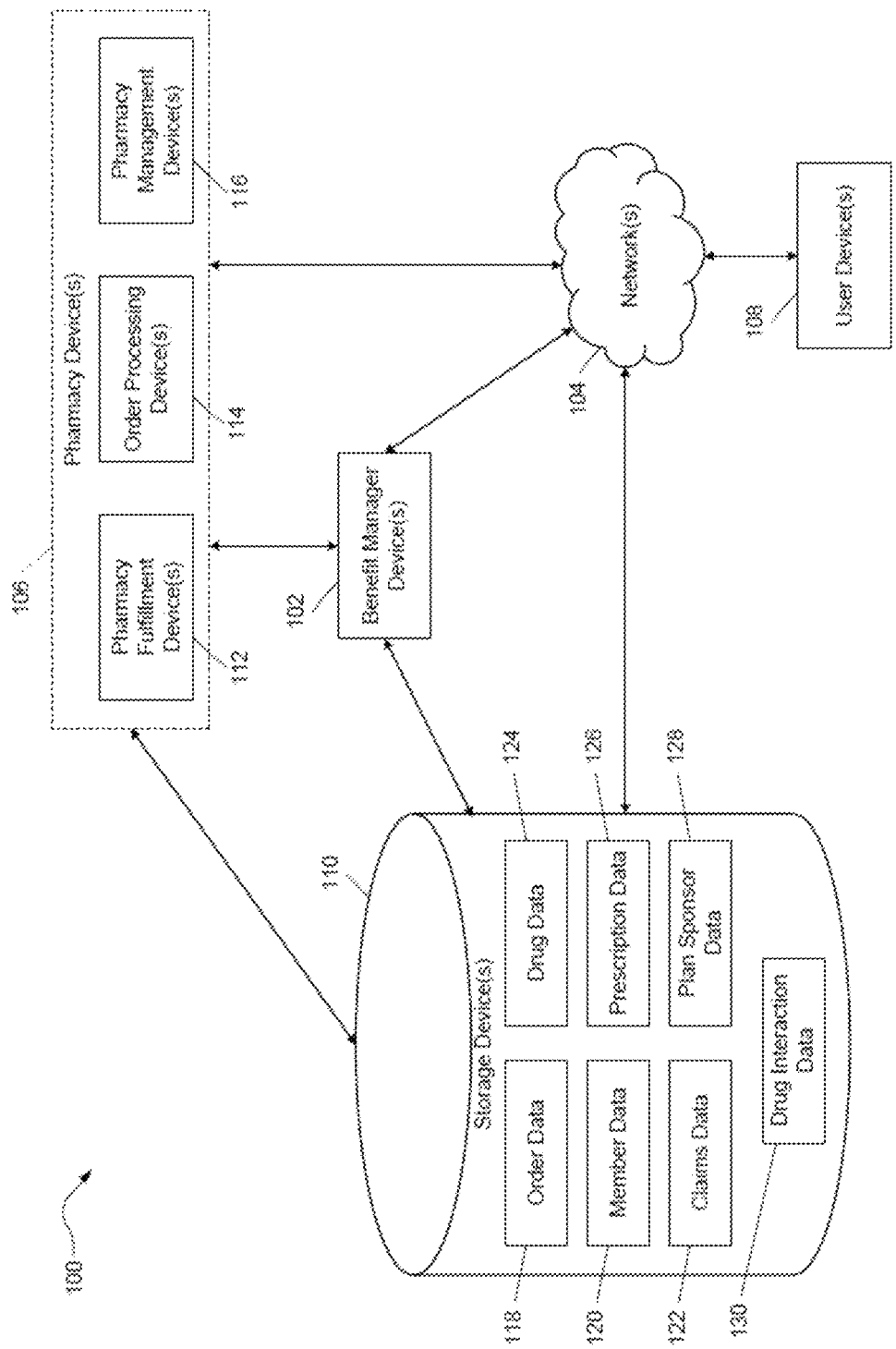
FIG. 1 is a functional block diagram of an example system including a high-volume pharmacy.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104. The system 100 may also include a storage device 110.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a rare genetic disease benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device 108, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The user device 108 may be a stand-alone device, or may be a multi-use device. Examples of the user device 108 include a set-top box (STB), a receiver card, a mobile telephone, a personal digital assistant (PDA), a display device, a portable gaming unit, and a computing system; however, other devices may also be used. For example, the user device 108 may include a mobile electronic device, such an IPHONE or IPAD device by Apple, Inc., mobile electronic devices powered by ANDROID by Google, Inc., and a BLACKBERRY device by Research In Motion Limited. The user device 108 also include other computing devices, such as desktop computing devices, notebook computing devices, netbook computing devices, gaming devices, and the like. Other types of electronic devices may also be used. Additionally or alternatively, the user device 108 can execute an application that may use a cellular phone function of the user device 108. The application may include instructions that when executed on the user device 108, in the benefit manager device 102, or pharmacy device 106, cause a machine to change its state or perform tasks within the machine and with other machines.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However, in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, exhaustion date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc. In addition, the member data 112 can include or reference prescription numbers associated with the member.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), typical dosing instructions, etc. The drug data 124 may include information associated with a single medication or multiple medications. However, dosing instructions may come from the claims data 122 if the doctor prescribed dosing instructions different from the typical dosing instructions.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

Furthermore, the drug interaction data 130 can include all known interactions between various prescription drugs. The known interactions can be negative, positive, or benign. Further still, the drug interaction data 130 can include known interactions between each prescription drug and over-the-counter drugs, known interactions between each prescription drug and vitamins or medical herbs (e.g. St. John's Wort), or known interactions between each prescription drug and commonly used substances, such as alcohol.

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
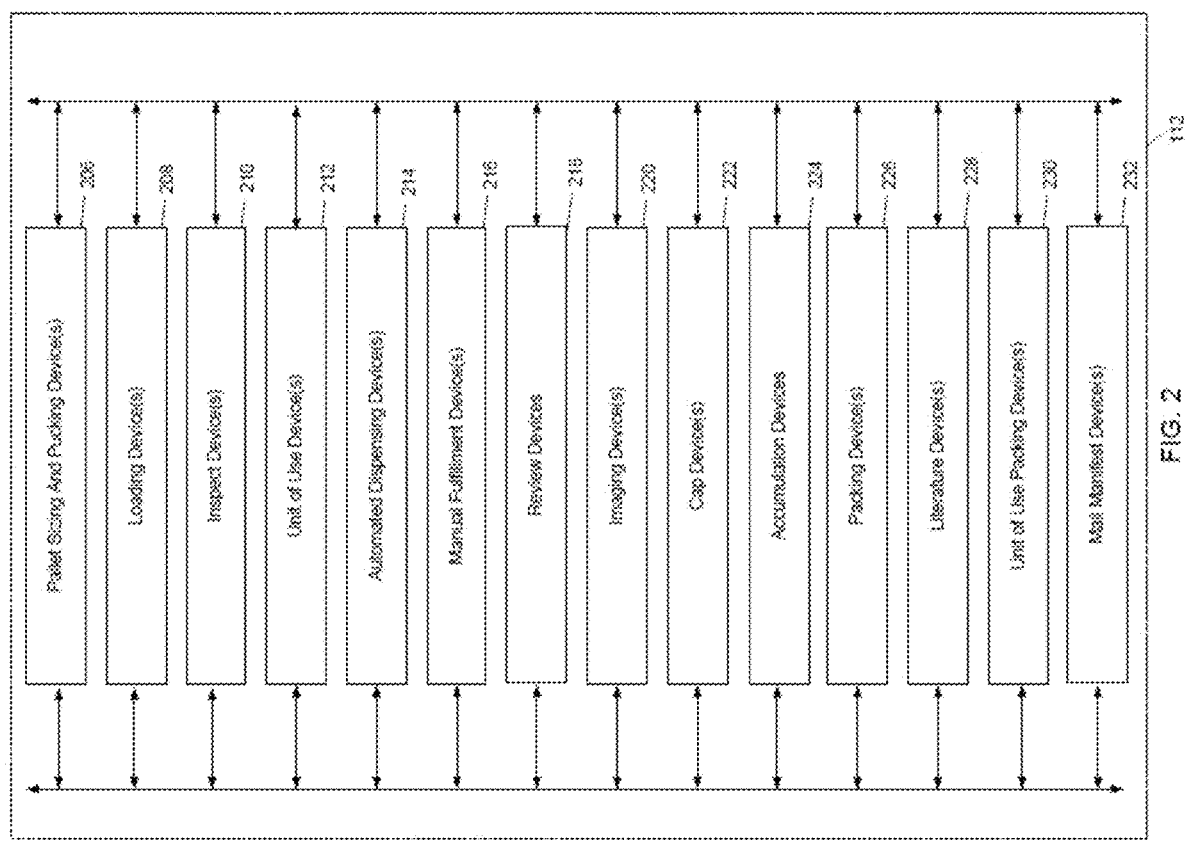
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
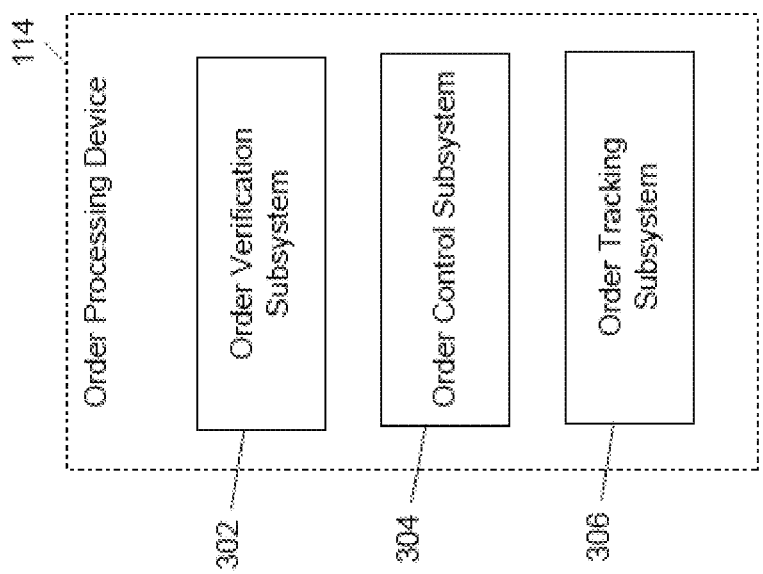
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Example methods and systems for managing prescription refills are described. More specifically, example methods and systems for synchronizing refill dates for certain prescriptions (e.g. maintenance drugs) are described. In the following description, for purposes of explanation, numerous specific details are set forth in order to provide a thorough understanding of example embodiments. It will be evident, however, to one of ordinary skill in the art that embodiments of the present disclosure may be practiced without these specific details.

Many clients of a PBM suffer from ailments that are considered chronic or long-term. Often, treatment of chronic or long-term diseases involves a drug therapy. Frequently, the drug therapy is not a cure but instead manages a disease or helps clients live with their ailment more comfortably. As such, many prescription drugs are taken daily or periodically (e.g. weekly, twice daily, monthly, etc.). Such drugs are considered maintenance drugs.

Because maintenance drugs must be taken regularly by clients, clients need these maintenance drugs periodically refilled so that they can continue with the drug therapy. Usually, for a maintenance drug, the day or time when a maintenance drug needs to be refilled is foreseeable by a pharmacy or a PBM. Thus, PBMs and pharmacies have begun offering automatic refills of maintenance drugs or other drugs that are regularly refilled. Clients have appreciated automatic refills because they do not need to request a refill in advance of running out of a medication. In a mail-order pharmacy environment, the automatic refill generally arrives in the mail a few days before the patient is set to run out of medication, whereas, in a traditional brick-and-mortar pharmacy environment, the prescription drug may be made available for pickup several days before the client is set to run out of medication. Either way, another fill of the maintenance medication is made available to the client before the client runs out of medications and without the client requesting the refill.

Commonly, PBM clients have been prescribed multiple maintenance medications. However, if the client has been prescribed multiple maintenance drugs, and the client is enrolled in automatic refills for all maintenance drugs, the date when a first prescription refill is mailed or made available at the pharmacy may not coincide with the date when a second prescription refill is mailed or made available. Unsynchronized refill dates for various medications can lead to customer annoyance (receiving too much mail from the PBM or requiring multiple trips to the pharmacy), generates unnecessary waste (redundant shipping boxes or plastic bags from the pharmacy), and additional cost to the client and PBM due to shipping and pharmacist time in filling all the prescription refills.

Figure 4:
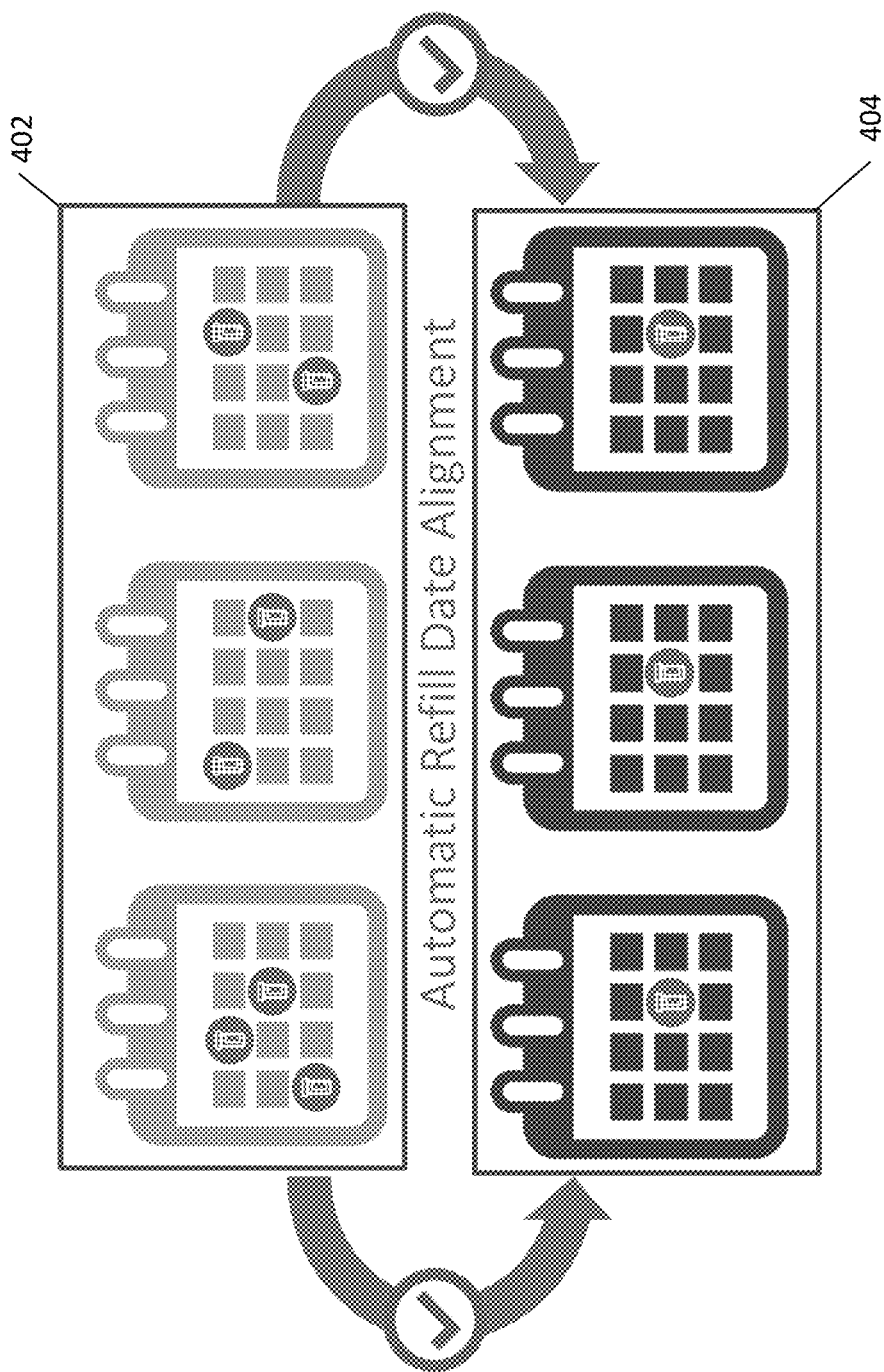
FIG. 4 is a block diagram of an example pharmacy benefit manager device that may be deployed within the system of FIG. 1, according to an example embodiment.

FIG. 4 illustrates this problem. Unsynchronized calendar 402 prior to medication synchronization according to the embodiments described herein shows multiple prescription refill dates scattered throughout a month and over a 90-day period. As such, a client could receive a medication refill as many as three times per month (or more), thereby requiring up to three (or more) refill shipments or three separate trips to the drug store. In contrast, after synchronization according to the methods described herein, the synchronized calendar 404 illustrates, at most, one refill per month (and possibly one refill per 90-day period). A client benefiting from the methods described herein would receive all maintenance drugs on the same date because all refill dates are synchronized.

One method for synchronizing refill dates would be to "short-fill" one or some of the plurality of prescriptions. A short-fill means that a pharmacy provided fewer or less than a full prescription fill. For example, if a typical refill includes 30 pills for a 30-day supply, a "short-fill" would include fewer than 30 fills. However, short-fills suffer from numerous problems. First, mechanical devices would need to be reprogramed to fill fewer than a normal amount of drugs, which could slow down fulfillment or cause errors in the short-fill or future prescription fills/refills. Alternatively, short-fills might confuse a patient expecting to receive a normal prescription refill.

Alternatively, another method of synchronization could provide more prescription than a typical refill. Again using the 30-pill example, this method could provide 45 pills. However, this method is even more undesirable because it suffers from all of the short-fill problems and also might violate drug laws or lead to drug abuse (e.g. overdose) by the client. Thus, there is needed a method for synchronizing prescription drugs without short-filling or over-filling a prescription drug refill.

Figure 5:
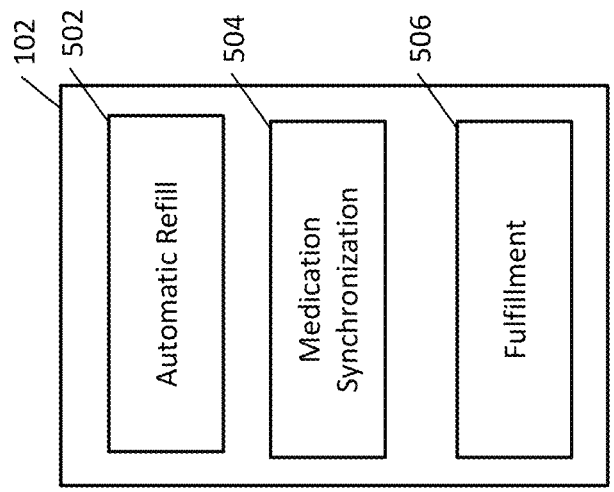
FIG. 5 is a block diagram of a flowchart illustrating methods for synchronizing prescription refills, according to an example embodiment.

FIG. 5 illustrates the benefit manager device 102, according to an example embodiment. The benefit manager device 102 may be deployed in the system 100 or may otherwise be used. While the benefit manager device 102 is described as storing and implementing the medication synchronization algorithm described herein, other devices in the system 100 could also implement the medication synchronization algorithm, such as the pharmacy fulfillment device 112, the order processing device 114 or the pharmacy management device 116.

The benefit manager device 102 may include an automatic refill subsystem 502, a medication synchronization subsystem 504, and a fulfillment subsystem 506. The automatic refills subsystem 502 can determine which clients and which prescriptions have enrolled or have been automatically enrolled in an automatic refill program. The automatic refill subsystem 502 may store all clients and all client's prescriptions that are enrolled in an automatic refill program in computer-readable memory, such as the storage device 110. In some embodiments, the refill enrollment data may be stored as member data 120, prescription data 126, or another data record stored by the storage device 110.

As used herein, an automatic refill program is a program provided by a PBM to automatically send or automatically make available a prescription drug refill at or near the time when a patient will run out of a current prescription drug fill without any customer interaction. In other words, when enrolled in an automatic re-fill program, the PBM can send or make available a prescription drug without the client or patient requesting the refill. In some embodiments, the automatic refill may automatically arrive or be made available 10-30 days before a current fill is set to run out (assuming the patient takes the prescription drug regularly exactly as prescribed).

For example, patients suffering from depression may receive a prescription (e.g. Sertraline to inhibit serotonin reuptake), and this prescription treatment may be taken daily as part of a maintenance medication therapy. Commonly, maintenance drug fills comprise a 90-day supply of the prescription drug, but maintenance drugs can be prescribed in other supply sizes (e.g. 30-day, 60-day, 7-day). In an automatic refill program, the PBM may, near the end of the first supply, mail a second supply of the maintenance drug to the patient a number of days before the first supply is set to run out due to the patient regularly taking the medication as prescribed (e.g. daily) when the patient is enrolled in an automatic refill program. Again, the refill is provided or made available to the client without the client requesting the refill or the doctor submitting another prescription. If the prescription is no longer valid (e.g. a doctor no longer approves the drug being taken by a patient), then the automatic refill program will not automatically refill the prescription.

In addition to storing the list of clients and prescriptions enrolled in an automatic refill program, the automatic refill subsystem 502 can also trigger automatic refills of a prescription drug when certain criteria are met. The criteria considered by the automatic refill subsystem 502 may include a date when the client is scheduled to run out of a current prescription fill (e.g. exhaustion date), whether the patient is enrolled in the automatic refill program, a date by which it is too soon to mail or make available a prescription drug refill ("Refill Too Soon Date" or "RTS"), the supply size of the current fill (30-day, 90-day, etc.), a date for mailing or making available the prescription drug (a "Worry Free Fill Date" or "WFF"), and others. In some embodiments, the automatic refill subsystem 502 may automatically mail or make available a refill on a predetermined number of days before the client is scheduled to run out of the current fill (e.g. 18 days before the client will run out of a 90-day supply, or 9 days before the client will run out of a 30 day supply, etc.). The WFF date may be determined according to a contract between a client and the pharmacy benefit manager, determined by Federal or State law, depend on a prescription from a prescribing doctor, or depend on patient preferences. In some embodiments, a patient may set the WFF date for each of the prescription drugs prescribed to them, so long as those preferences comply with a benefit plan and Local and Federal Law. Regardless, the WFF date is a date before the patient runs out of medication and usually several days or weeks before the patient is scheduled to run out of medication. Additionally, in a mail-order pharmacy embodiment, the automatic refill subsystem 502 may consider a time for the prescription drug to arrive at the client's shipping address in calculating when to trigger an automatic refill. In some embodiments, triggering an automatic refill may involve sending an instruction to the pharmacy fulfillment device 112 to refill a prescription and mail or make available the prescription. The automatic refill subsystem 502 may also transmit a message (email, text message, etc.) to the client notifying them that the prescription drug is being automatically refilled. In some embodiments, the patient can cancel the automatic refill in response to this message.

Further still, the automatic refill subsystem 502 can perform the adjudication functions described above as part of the refill determination. Adjudication in the refill context can additionally include identifying whether the patient is still eligible to receive the prescription drug as a refill, determining whether refilling the prescription drug would trigger any adverse drug reactions to newly prescribed drugs, and performing the DUR described above. In some embodiments, the DUR can identify the RTS date and the WFF day.

According to an exemplary embodiment, the benefit manager device 102 may further include a medication synchronization subsystem 504 implementing a medication synchronization algorithm. The medication synchronization subsystem 504 determines whether two or more prescription drugs enrolled in the automatic refill program can be mailed or made available at the same time. In the mail-order pharmacy embodiment, the medication synchronization subsystem 504 may further determine that the two or more prescription drugs can be mailed together in the same box or envelope to reduce shipping strain, reduce waste, and lower costs. Furthermore, because the medication synchronization subsystem 504 determines that multiple prescription drugs can be refilled concurrently, the amount of processing performed by the automatic refill subsystem 502 and the benefit manager device 102 as a whole is lowered because it does not need to identify and trigger automatic refills for all prescription drugs individually. Therefore, the medication synchronization subsystem 504 not only improves a client's user experience, the medication synchronization subsystem 504 improves the computing performance of the benefit manager device 102. Additionally, the benefit manager device 102 conducts fewer online transaction with the post office or shipping providers because fewer boxes or envelopes are mailed.

Finally, the fulfillment subsystem 506 can identify the necessary parameters to refill the prescription drug, including generating instructions for the pharmacy in filling the prescription. In the mail-order or high-volume pharmacy embodiment, the fulfillment subsystem may generate the necessary commands to the order processing device 114 so that the order processing device 114 can automatic fill or refill of the prescription drug. In the traditional, brick-and-mortar example, the fulfillment subsystem 506 may generate written instructions for a pharmacist to read when refilling the prescription drug. In some embodiments, the functions of the fulfillment subsystem 506 can be performed entirely in the order processing device 114, and the automatic refill subsystem 502 and the medication synchronization subsystem 504 can communicate with the fulfillment subsystem 506 over the network 104.

In response to identifying that two or more prescription drugs enrolled in the automatic refill program can be mailed or made available at the same time, the medication synchronization subsystem 504 will instruct the fulfillment subsystem 506 to mail together the two or more prescription drugs or make available the two or more prescription drugs at the same time.

Figure 6A:
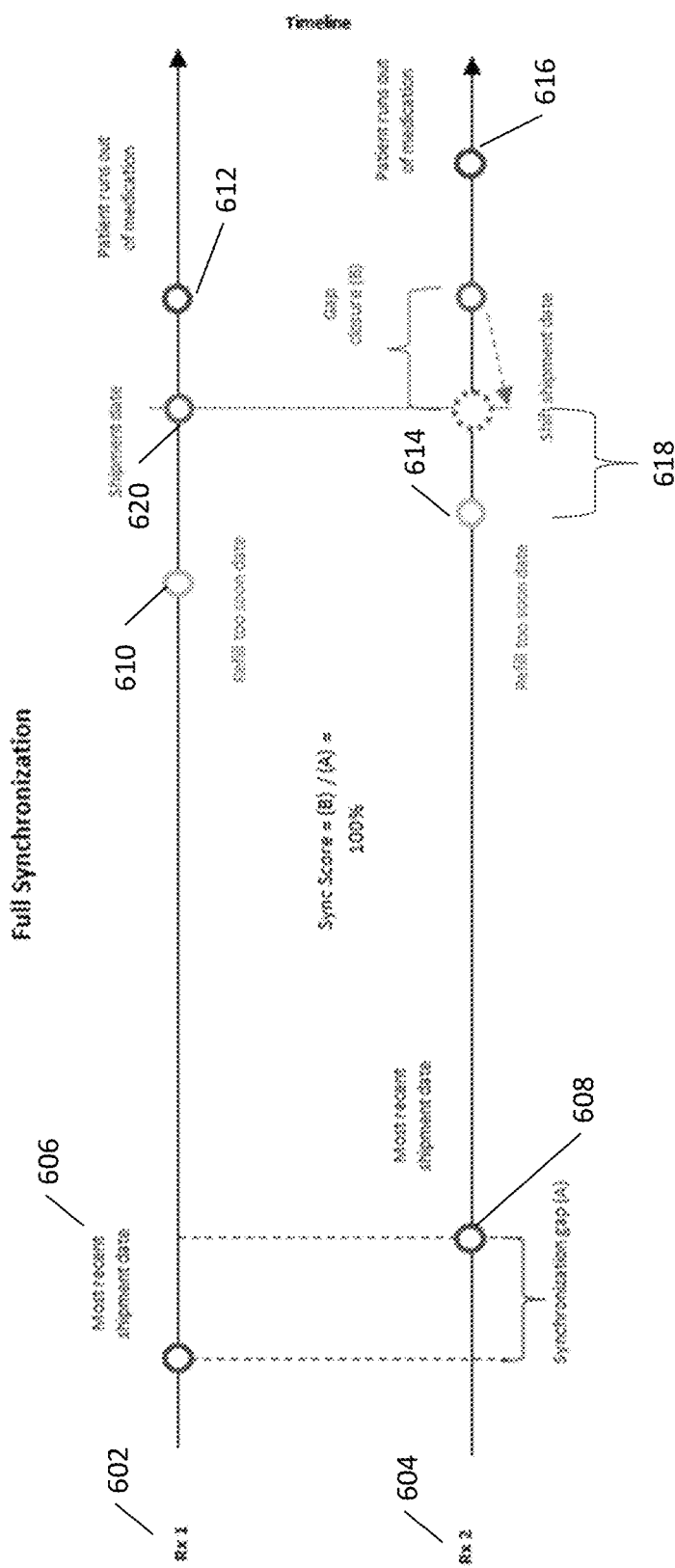
FIGS. 6A and B are block diagrams illustrating various parameters and guideposts considered when synchronizing prescription refills, according to an example embodiment.

In considering whether two or more prescription refills can be mailed or made available at the same time, the medication synchronization subsystem 504 considers three "guideposts", between which can include an "opportunity window", under the right conditions. Additional prescriptions can be mailed or made available at the same time if each prescription refill can be mailed or made available within the opportunity window. FIG. 6A illustrates these guideposts and the opportunity window according to an exemplary embodiment.

FIG. 6A illustrates timelines for a first prescription drug 602 and a second prescription drug 604. As shown, the first prescription drug 602 was mailed a few days earlier than the second prescription drug 604, meaning that the first prescription drug 602 was previously mailed on a first historical shipment date 606, and the second prescription drug 604 was mailed on a second historical shipment date 608, and the second historical shipment date 608 occurred after the first historical shipment date 606. Because the first prescription drug 602 has a different historical shipment date 606 than the second historical shipment date 608 of the second prescription drug 604, the PBM mailed the first prescription drug 602 in a different box or envelop than the second prescription drug 604, and thereby paid for two shipments (or the PBM made the first prescription drug 602 available on a different date than the second prescription drug 604, potentially leading to two, redundant trips for the client to the pharmacy).

As explained above, the medication synchronization subsystem 504 calculates an RTS date and a date when the patient will run out of medication ("exhaustion date"). The RTS date may be calculated based on one or a number of factors including Federal and State law, instructions from a doctor, prescription benefit plan terms, or the like. For example, some benefit plans call for a patient to always have taken 66% of medication before a refill is allowed, others call for 75%; these parameters can also be used to calculate the RTS date. The RTS date and the exhaustion date can depend on the historical shipment date of a prescription drug. Thus, the first prescription drug has a first RTS date 610 and a first exhaustion date 612 calculated from the first historical shipment date 606, and the second prescription drug has a second RTS date 614 and a second exhaustion date 616 calculated from the second historical shipment date 608. If the second RTS date 614 occurs after the first RTS date and before a first future shipment date 620, then an opportunity window 618 can be created. In some embodiments, the opportunity window 618 can comprise the time window between the second RTS date 614 and the first future shipment date 620 (which is the WFF date). If the second RTS date 614 occurs before the first future shipment date 620 and after the first RTS date 610, then the PBM can advance the second prescription's second shipment date to coincide with the first future shipment date 620 so that both medications 602, 604 are shipped together. According to the exemplary embodiments, a full refill (e.g. full 30-day or 90 day supply) for both the first and second prescription drugs is shipped (together), and neither drug is refilled as a short fill or an overfill.

Additionally, the exemplary embodiments can perform similar or repeated analysis with more than two prescription drugs in an attempt to synchronize as many drugs as possible.

While the exemplary embodiments have so far been described in the context of refills, the exemplary embodiments also envision a similar situation with a new prescription. In this scenario, the exemplary embodiments will consider whether the new prescription drug fill was ordered after the RTS date 610 and before the shipment date 620 of the automatically refilled prescription drug 602. If so, the medication synchronization subsystem 504 can move up the shipment date of the automatically refilled prescription drug 602 to coincide with the shipment date of the new prescription fill.

Figure 6B:
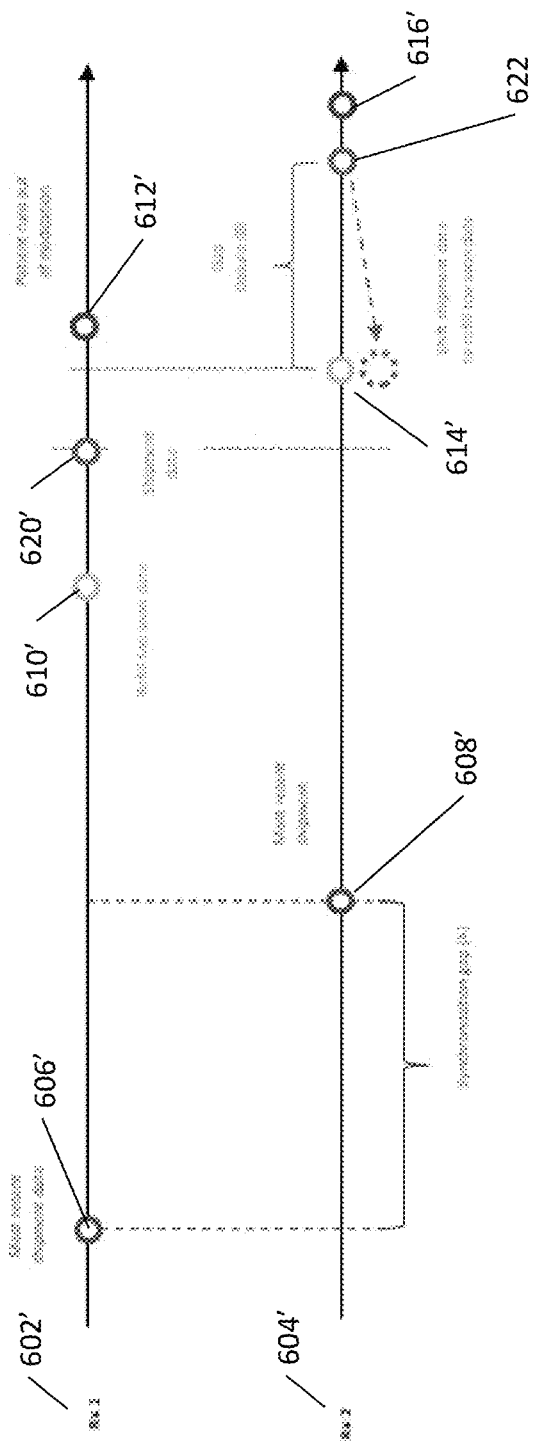

FIG. 6A illustrates a particularly fortunate scenario where the second RTS date 614 occurs after the first RTS date and before the first exhaustion date 612 (or before the first prescription's second shipment date 620). However, this may not always occur. As such, it may take multiple refill iterations to fully synchronize the shipment date of two or more prescription drugs. FIG. 6B illustrates a multiple iteration synchronization process. Like before, the first prescription drug 602' has a first historical shipment date 606', a first RTS date 610', a first future shipment date 620', and a first exhaustion date 612', and the second prescription drug 604' has a second historical shipment date 608', a second RTS date 614', a second future shipment date 622, and a second exhaustion date 616'. However, in the scenario shown in FIG. 6B, no opportunity window exists because the second RTS date 614' occurs after the first future shipment date 620'. While the two prescription drugs 602', 604' cannot be synchronized in this refill iteration, the second prescription drug's ship date 622 can still be advanced to the second RTS date 614', as shown. Because the second shipment date 622 was advanced, a future RTS date for the second prescription drug 604' can also advance and provide an opportunity window in a future refill iteration. This advancement of the second prescription drug's ship date 622 can continue until the two drugs are synchronized.

Figure 7:
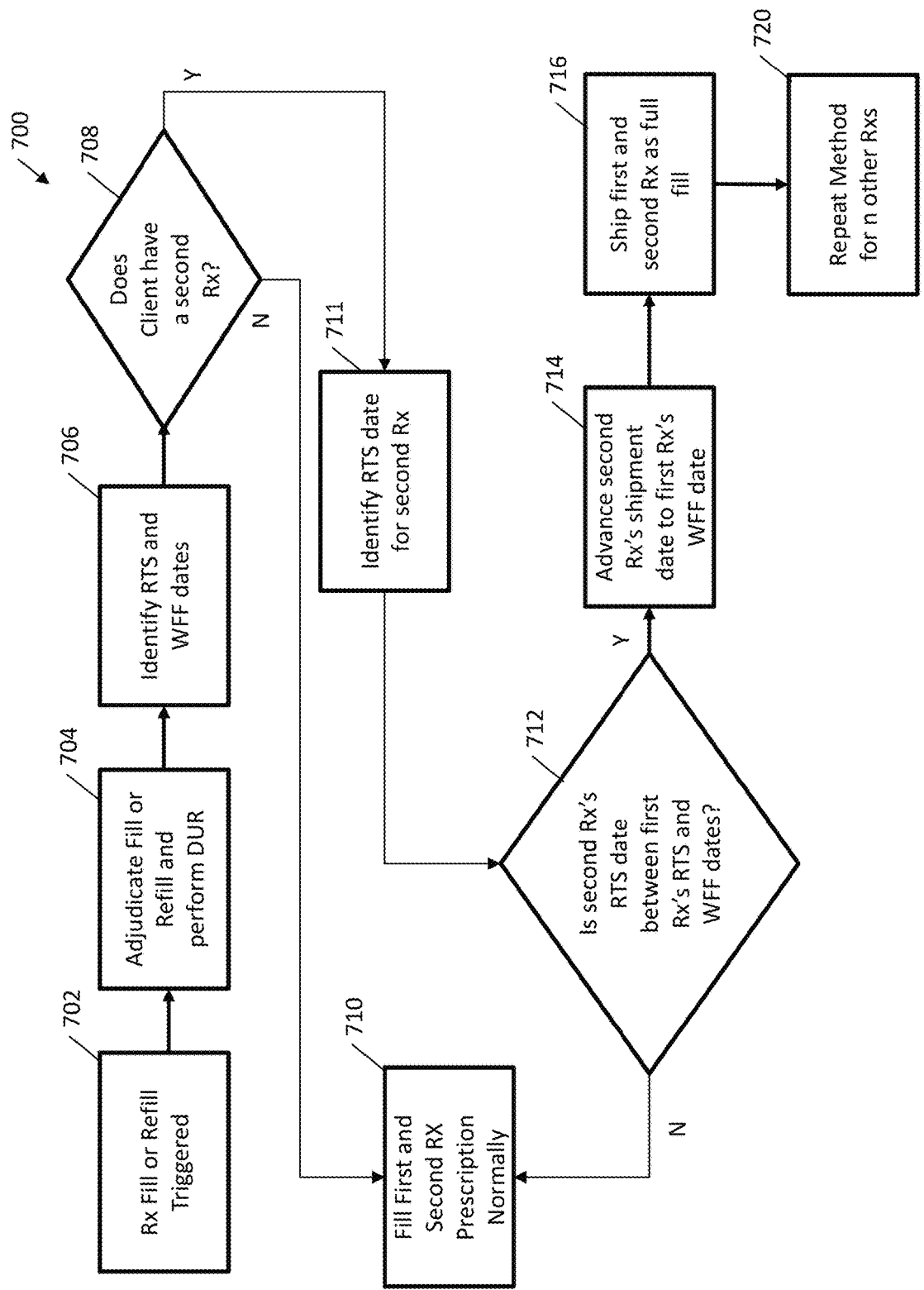
FIG. 7 is a block diagram of a flowchart illustrating methods for synchronizing multiple refills, according to an example embodiment

FIG. 7 illustrates a method 700 for synchronizing a shipment or availability date of multiple prescriptions according to an example embodiment. The method 700 may be performed by the pharmacy device 106, by the benefit manager device 102, partially by the benefit manager device 102 and partially by the pharmacy device 106, or may be otherwise performed. For the sake of simplicity, the benefit manager device 102 will be described as performing the steps of the method 700, but the embodiments described herein are not so limited.

According to an exemplary embodiment, the benefit manager device 102 can identify that a first prescription drug should be filled or refilled for a client in step 702. According to an exemplary embodiment, step 702 may occur as part of an automatic refill program, as described above in depth, but step 702 may also be related to a new prescription drug fill request from a client. Such a request may come from a pharmacy or the user device 108.

After identifying that the first prescription drug is to be filled or refilled, the benefit manager device 102 can adjudicate a prescription claim associated with the first prescription drug in step 704. The process for claim adjudication was described in detail above and can include determining a co-payment amount and an amount covered by insurance. Furthermore, adjudication can involve the DUR discussed above, which can include determining whether the first prescription drug will adversely interact or react with other prescriptions or supplements taken by the client. As part of the DUR, the benefit manager device 102 can identify a first guidepost date (e.g. the RTS date) and a second guidepost date (e.g. the WFF or drug exhaustion date) associated with the first prescription drug in step 706.

Subsequently, the benefit manager device 102 can identify whether the client has been prescribed a second prescription drug in step 708. In some embodiments, benefit manager device 102 can identify that the client has been prescribed a second prescription drug by determining that the client has multiple prescriptions enrolled in the automatic refill program or another drug enrolled in the automatic refill program. In some embodiments, the benefit manager device 102 can determine whether the client has been prescribed a second prescription drug that is not enrolled in the automatic refill program but is eligible for enrollment in the automatic refill program. Regardless, in step 708, the benefit manager device 102 can identify whether the client is associated with any other prescription drugs to be filled or refilled in the future.

If the client has not been prescribed any other prescription drugs, then the benefit manager device 102 can instruct the pharmacy device 106 to fill and dispense the first prescription drug according to traditional methods on or before the second guidepost date (e.g. on the WFF date) in step 710. In some embodiments, dispensing the drug can include shipping the drug to the client via the mail or other shipment method. Additionally, during step 710, the benefit manager device 102 can instruct the pharmacy device 106 to fill and dispense the second prescription drug according to traditional methods on or before a WFF date for the second prescription drug.

If the client has been prescribed more than one prescription drug, the benefit manager device 102 can identify a third guidepost date (e.g. second prescription drug's RTS) associated with the second prescription drug in step 711. Subsequently, the benefit manager device 102 compares the third guidepost date (e.g. second prescription drug's RTS) to the first and second guidepost dates (first prescription drug's RTS and WFF or exhaustion dates) to determine whether the third guidepost date occurs after the first guidepost date and before the second guidepost date in step 712.

If the third guidepost date does not occur after the first guidepost date and before the second guidepost date, the benefit manager device fills and dispenses the first prescription drug according to traditional methods on or before the second guidepost date (e.g. on the WFF date) in step 710. However, if the third guidepost date does occur after the first guidepost date and before the second guidepost date, the benefit manager device 102 advances the fill and dispensing date for the second prescription drug to the second guidepost date in step 714 and fills and dispenses the first and second prescription drug on the same day in step 716. In some embodiments, filling and dispensing the first and second prescription drugs together can include shipping the first and second prescription drug to the client via the mail or other shipment method in the same box or envelop. Furthermore, in some embodiments, filling and dispensing the first and second prescription drugs can include providing full supplies for both prescription drugs (e.g. both 90-day supplies).

The method 700 can repeat for a third, fourth, or nth prescription drug prescribed to the same patient in an attempt to synchronize as many drugs as possible in step 720.

Figure 8:
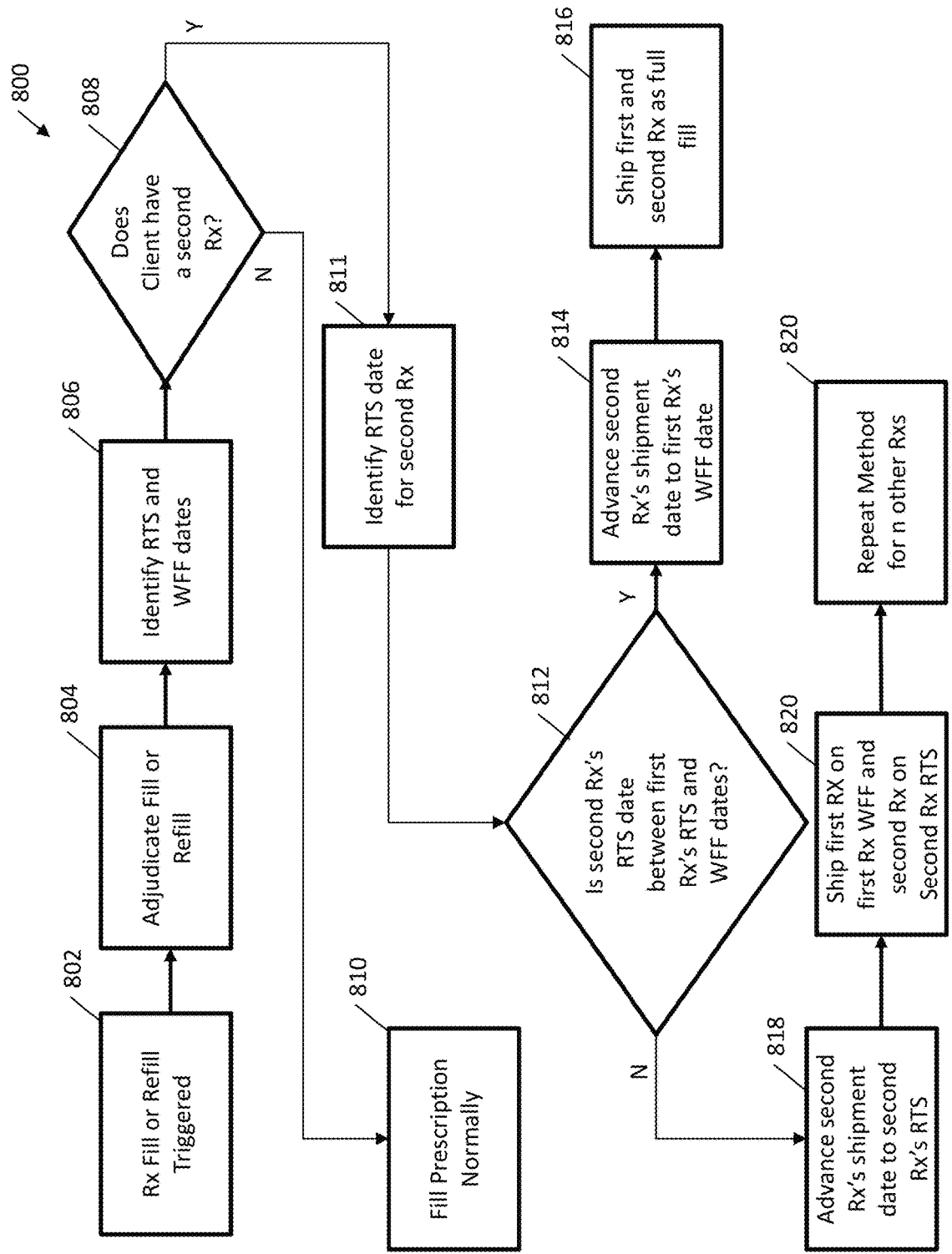
FIG. 8 is a block diagram of a flowchart illustrating methods for partial and full synchronization of multiple refills, according to an example embodiment

FIG. 8 illustrates a method 800 for partially or fully synchronizing a shipment or availability date of multiple prescriptions according to an example embodiment. The method 800 may be performed by the pharmacy device 106, by the benefit manager device 102, partially by the benefit manager device 102 and partially by the pharmacy device 106, or may be otherwise performed. For the sake of simplicity, the benefit manager device 102 will be described as performing the steps of the method 800, but the embodiments described herein are not so limited.

According to an exemplary embodiment, the benefit manager device 102 can identify that a first prescription drug should be filled or refilled for a client in step 802. According to an exemplary embodiment, step 802 may occur as part of an automatic refill program, as described above in depth, but step 802 may also be related to a new prescription drug fill request from a client. Such a request may come from a pharmacy or the user device 108.

After identifying that the first prescription drug is to be filled or refilled, the benefit manager device 102 can adjudicate a prescription claim associated with the first prescription drug in step 804. The process for claim adjudication was described in detail above and can include determining a co-payment amount and an amount covered by insurance. Furthermore, adjudication can involve the DUR discussed above, which can include determining whether the first prescription drug will adversely interact or react with other prescriptions or supplements taken by the client. As part of the DUR, the benefit manager device 102 can identify a first guidepost date (e.g. the RTS date) and a second guidepost date (e.g. the WFF or drug exhaustion date) associated with the first prescription drug in step 806.

Subsequently, the benefit manager device 102 can identify whether the client has been prescribed a second prescription drug in step 808. In some embodiments, benefit manager device 102 can identify that the client has been prescribed a second prescription drug by determining that the client has multiple prescriptions enrolled in the automatic refill program or another drug enrolled in the automatic refill program. In some embodiments, the benefit manager device 102 can determine whether the client has been prescribed a second prescription drug that is not enrolled in the automatic refill program but is eligible for enrollment in the automatic refill program. Regardless, in step 808, the benefit manager device 102 can determine whether the client is associated with any other prescription drugs to be filled or refilled in the future.

If the client has not been prescribed any other prescription drugs, then the benefit manager device 102 instructs the pharmacy device 106 to fill and dispense the first prescription drug according to traditional methods on or before the second guidepost date (e.g. on the WFF date) in step 810. In some embodiments, dispensing the drug can include shipping the drug to the client via the mail or other shipment method.

If the client has been prescribed more than one prescription drug, the benefit manager device 102 can identify a third guidepost date (e.g. second prescription drug's RTS) associated with the second prescription drug in step 811. Subsequently, the benefit manager device 102 compares the third guidepost date (e.g. second prescription drug's RTS) to the first and second guidepost dates (first prescription drug's RTS and WFF or exhaustion dates) to determine whether the third guidepost date occurs after the first guidepost date and before the second guidepost date in step 812.

If the third guidepost date occurs after the first guidepost date and before the second guidepost date, the benefit manager device 102 advances the fill and dispensing date for the second prescription drug to the second guidepost date in step 814 and fills and dispenses the first and second prescription drug on the same day. In some embodiments, filling and dispensing the first and second prescription drugs together can include shipping the first and second prescription drug to the client via the mail or other shipment method in the same box or envelop in step 816. Furthermore, in some embodiments, filling and dispensing the first and second prescription drugs can include providing full supplies for both prescription drugs (e.g. both 90-day supplies).

However, if the third guidepost date does not occur after the first guidepost date and before the second guidepost date, the benefit manager device advances the fill and dispensing date for the second prescription drug to the third guidepost date (second prescription's RTS) in step 818. In some embodiments, the benefit manager device 102 can ships first prescription drug on the second guidepost date and ships the second prescription drug on the third guidepost date in step 820. Even though the first and second prescription drugs are shipped on different days, through the method 800, the shipment dates for the first and second prescriptions are moved closer together, and full synchronization can occur on a future refill iteration.

The method 800 can repeat for a third, fourth, or nth prescription drug prescribed to the same patient in an attempt to synchronize as many drugs as possible in step 820.

While the methods 700 and 800 were described using an exemplary two prescriptions, the methods 700 and 800 can be repeated to synchronize more than two prescription drugs. Furthermore, in the embodiment where the first prescription drug is a new prescription, the new prescription will only have a fill date, and the benefit manager device 102 will determine whether the second prescription drug's RTS occurred before the first prescription's fill date but before the second prescription's WFF date. If so, the benefit manager device 102 will advance the second prescriptions refill date to coincide with the first prescription's fill date.

The claimed systems and methods optimize a high-volume, mail-order pharmacy in terms of shipping prescriptions to customers because the high-volume, mail-order pharmacy can ship more prescriptions using less packaging (boxes, envelopes, etc.) and purchasing fewer shipping labels from shipping companies (USPS, UPS, FedEx, etc.). This optimization not only minimizes costs but also is better for the environment as less packaging is needed to ship the same amount of prescription drugs. In addition, the high-volume, mail-order pharmacy can process more prescription drugs at the packing stage of the high-volume, mail-order pharmacy. Because the packing device can pack multiple drugs into one package, the packing device becomes more efficient in packing drugs. All these improvements result in an optimized high-volume, mail-order pharmacy.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

The invention claimed is:

1. A system comprising:
a processor configured to (a) identify that a first prescription drug prescribed to a first patient should be filled by a pharmacy, (b) identify a first guidepost date and a second guidepost date related to the first prescription drug, the second guidepost date occurring after the first guidepost date, and both the first and second guidepost dates depending on a previous fill of the first prescription drug, (c) identify a third guidepost date associated with a second prescription, and (d) compare the third guidepost date to the first and second guidepost dates to determine whether the third guidepost date occurs after the first guidepost date and before the second guidepost date;
an automated dispenser configured to automatically fill and dispense the first prescription drug as a full prescription supply and the second prescription drug as the full prescription supply on the same dispense date in response to a command from the processor; and a packager configured to pack and ship the first prescription drug and the second prescription drug in one packaging item when the third guidepost date occurs after the first guidepost date and before the second guidepost date.

2. The system of claim 1 wherein the processor is further configured to:

generate an instruction to ship the second prescription drug on the second guidepost date with the first prescription drug when the third guidepost date occurs after the first guidepost date and before the second guidepost date.

3. The system of claim 1 wherein the first guidepost date is a date by which it is too soon to fill and dispense the first prescription drug, and wherein the third guidepost date is a final date by which it is too soon to fill and dispense the second prescription drug.

4. The system of claim 1 wherein the third guidepost date is a date when second prescription drug is scheduled to be shipped or made available to a client.

5. The system of claim 4 wherein the full prescription supply comprises a 90-day supply of the first and second prescription drugs.

6. The system of claim 1 wherein the second guidepost is a date when a client is scheduled to run out of the first prescription drug.

7. The system of claim 1 wherein the one packaging item is a single envelop or a single box.

8. The system of claim 1 wherein the processor determines the third guidepost date by being further configured to:

determine whether a client has been prescribed the second prescription drug;

identify that the second prescription drug is enrolled in an automatic refill program; and access the third guidepost date associated with the second prescription drug when the client has been prescribed the second prescription drug.

9. The system of claim 1 wherein the processor determines the third guidepost date by being further configured to:

determine whether a client has been prescribed the second prescription drug, wherein the second prescription drug is a newly prescribed drug;

identify that the second prescription drug is enrolled in an automatic refill program; and identify the third guidepost date based on when the newly prescription drug should arrive to the client.

10. The system of claim 1 wherein the processor is further configured to:

identify a fourth guidepost date associated with a third prescription drug;

compare the fourth guidepost date to the first and second guidepost dates to determine whether the fourth guidepost date occurs after the first guidepost date and before the second guidepost date; and fill and dispense the third prescription drug as the full prescription supply on the same dispense date when the third guidepost date occurs after the first guidepost date and before the second guidepost date, the third prescription drug being filled and dispense together with the first and second prescription drugs.

11. The system of claim 1, wherein the same dispense date comprises the second guidepost date.

12. The system of claim 11, wherein when the third guidepost date does not occur after the first guidepost date and before the second guidepost date, the processor is further configured to:

fill and dispense the first prescription drug as the full prescription supply on the second guidepost date;

advance a shipment or availability date for the second prescription drug to the third guidepost date; and fill and dispense the second prescription drug as the full prescription supply on the third guidepost date.

13. The system of claim 12 wherein the processor is configured to (a) again identify that the first prescription drug prescribed to the first patient should be filled by the pharmacy in a subsequent drug refill period of time, (b) identify a fifth guidepost date and a sixth guidepost date related to the first prescription drug, the sixth guidepost date occurring after the fifth guidepost date, and both the fifth and sixth guidepost dates depending on the dispense date of the first prescription drug, (c) identify a seventh guidepost date associated with the second prescription, and (d) compare the seventh guidepost date to the fifth and sixth guidepost dates to determine whether the seventh guidepost date occurs after the fifth guidepost date and before the sixth guidepost date;

wherein the automatic dispenser fills and dispenses the first prescription drug as the full prescription supply and the second prescription drug as the full prescription supply on a subsequent same dispense date during the subsequent drug refill period of time.

14. A method comprising identifying, at a processor, that a first prescription drug prescribed to a first patient should be filled by a pharmacy;

identifying, at the processor, a first guidepost date and a second guidepost date related to the first prescription, the second guidepost date occurring after the first guidepost date, both the first and second guidepost dates depending on a previous fill of the first prescription drug;

identifying, at the processor, a third guidepost date associated with a second prescription;

comparing, at the processor, the third guidepost date to the first and second guidepost dates to determine whether the third guidepost date occurs after the first guidepost date and before the second guidepost date; and filling and dispensing the first prescription drug as a full prescription supply and the second prescription drug as the full prescription supply on the same dispense date when the third guidepost date occurs after the first guidepost date and before the second guidepost date.

15. The method of claim 14 further comprising:

generating, at the processor, an instruction to ship the second prescription drug on the second guidepost date with the first prescription drug when the third guidepost date occurs after the first guidepost date and before the second guidepost date.

16. The method of claim 15 wherein the first and second prescription drugs are shipped to a client together in the same box or envelope.

17. The method of claim 14 wherein the first guidepost date is a date by which it is too soon to fill and dispense the first prescription drug, and wherein the third guidepost date is a date by which it is too soon to fill and dispense the second prescription drug.

18. The method of claim 14 wherein the third guidepost date is a date when second prescription drug is scheduled to be shipped or made available to a client.

19. The method of claim 14 wherein the second guidepost is a date when a client is scheduled to run out of the first prescription drug.

20. The method of claim 14 wherein the full prescription supply comprises a 90-day supply of the first and second prescription drugs.

21. The method of claim 14 wherein identifying the third guidepost date comprises:
determining, at the processor, whether a client has been prescribed the second prescription drug;
identifying, at the processor, that the second prescription drug is enrolled in an automatic refill program; and
accessing, at the processor, the third guidepost date associated with the second prescription drug when the client has been prescribed the second prescription drug.

22. The method of claim 14 wherein identifying the third guidepost date comprises:
determining, at the processor, whether a client has been prescribed the second prescription drug, wherein the second prescription drug is a newly prescribed drug;
identifying, at the processor, that the newly prescribed drug is enrolled in an automatic refill program; and
identifying, at the processor, the third guidepost date based on when the newly prescribed drug should arrive to the client.

23. The method of claim 14 further comprising:
identifying, at the processor, a fourth guidepost date associated with a third prescription drug;
comparing, at the processor, the fourth guidepost date to the first and second guidepost dates to determine whether the fourth guidepost date occurs after the first guidepost date and before the second guidepost date; and
filling and dispensing the third prescription drug as the full prescription supply on the same dispense date when the third guidepost date occurs after the first guidepost date and before the second guidepost date, the third prescription drug being filled and dispense together with the first and second prescription drugs.

24. The method of claim 14, wherein automated machinery fills and dispenses the first and second prescription drugs.

25. The method of claim 14, wherein the same dispense date comprises the second guidepost date.

26. The method of claim 14 further comprising, when the third guidepost date does not occur after the first guidepost date and before the second guidepost date:
filling and dispensing the first prescription drug as the full prescription supply on the second guidepost date;
advancing, at the processor, a shipment or availability date for the second prescription drug to the third guidepost date; and
filling and dispensing the second prescription drug as the full prescription supply on the third guidepost date.

27. The method of claim 26 further comprising:
again identifying that the first prescription drug prescribed to the first patient should be filled by the pharmacy in a subsequent drug refill period of time;
identifying a fifth guidepost date and a sixth guidepost date related to the first prescription drug, the sixth guidepost date occurring after the fifth guidepost date, and both the fifth and sixth guidepost dates depending on the dispense date of the first prescription drug;
identifying a seventh guidepost date associated with the second prescription; and
comparing the seventh guidepost date to the fifth and sixth guidepost dates to determine whether the seventh guidepost date occurs after the fifth guidepost date and before the sixth guidepost date;
filling and dispensing the first prescription drug as the full prescription supply and the second prescription drug as the full prescription supply on a subsequent same dispense date during the subsequent drug refill period of time.

28. A non-transitory machine-readable medium comprising instructions, which, when executed by one or more processors, cause the one or more processors to perform the following operations:
identify that a first prescription drug prescribed to a first patient should be filled by a pharmacy;
identify a first guidepost date and a second guidepost date related to the first prescription, the second guidepost date occurring after the first guidepost date, and both the first and second guidepost dates depending on a previous fill of the first prescription drug;
identify a third guidepost date associated with a second prescription;
compare the third guidepost date to the first and second guidepost dates to determine whether the third guidepost date occurs after the first guidepost date and before the second guidepost date; and
generate an instruction for a high-volume fulfillment center to fill and dispense the first prescription drug as a full prescription supply and the second prescription drug as a full prescription supply on the same dispense date when the third guidepost date occurs after the first guidepost date and before the second guidepost date.

* * * * *